Figure 1:
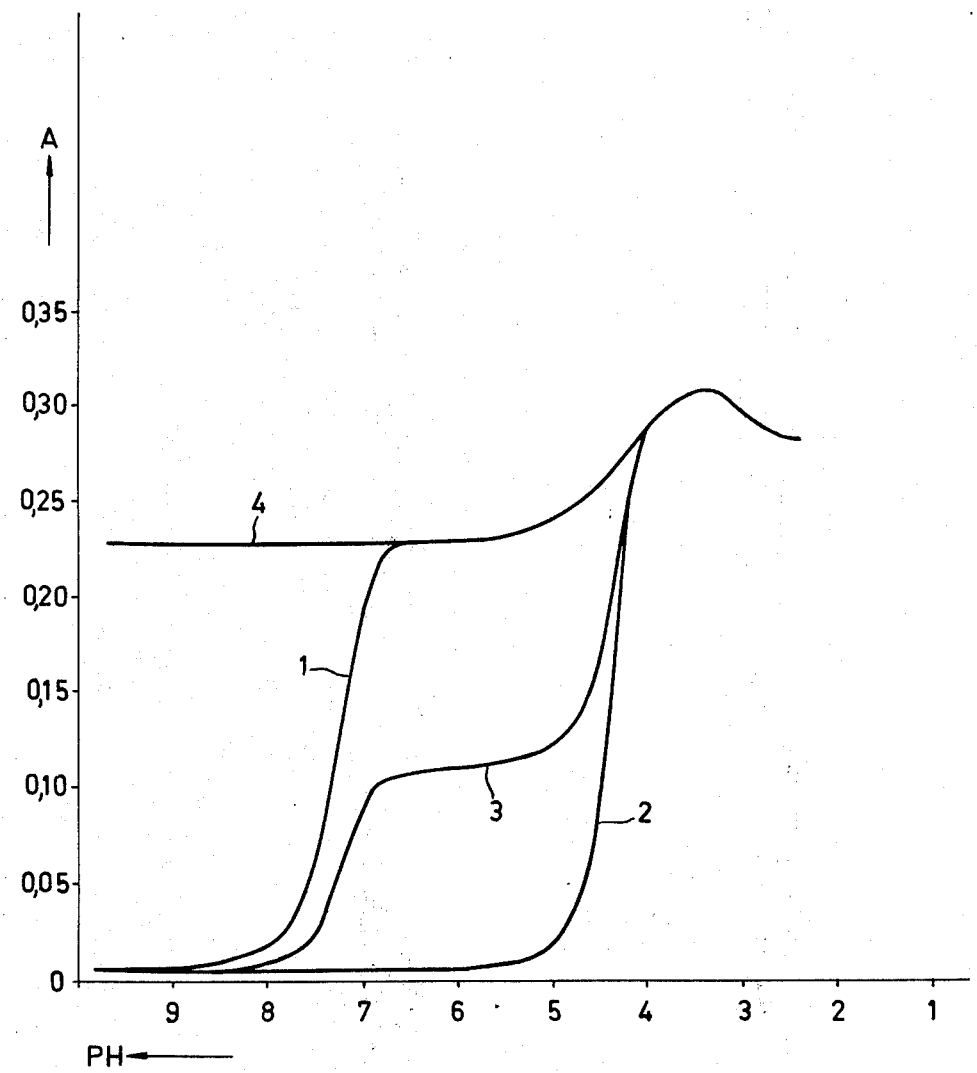

United States Patent [19]
Kloosterboer

[11] 3,972,680
[45] Aug. 3, 1976

[54] DIFFERENTIALLY KINETIC DETERMINATION OF METAL IONS

[75] Inventor: Johan George Kloosterboer, Eindhoven, Netherlands

[73] Assignee: U.S. Philips Corporation, New York, N.Y.

[22] Filed: Feb. 3, 1975

[21] Appl. No.: 546,397

[30] Foreign Application Priority Data
Feb. 7, 1974 Netherlands .................. 7401675

[52] U.S. Cl. .................................. 23/230 R
[51] Int. Cl.² .............. G01N 33/00; G01N 33/16; G01N 33/18
[58] Field of Search ....................... 23/230 R

[56] References Cited
OTHER PUBLICATIONS
Pausch et al., Anal. Chem., 41, 226, (1969).
Margerum et al., Anal. Chem., 41, 233, (1969).

Primary Examiner—Robert M. Reese
Attorney, Agent, or Firm—Frank R. Trifari; Norman N. Spain

[57] ABSTRACT

Differentially kinetic determination of metal ions using metal complexes of trans-1,2-diaminocyclohexane-N,N,N',N'-tetra-acetate.

5 Claims, 2 Drawing Figures

DIFFERENTIALLY KINETIC DETERMINATION OF METAL IONS

The invention relates to a method for differentially kinetic determination of metal ions while using metal complexes of trans-1,2-diaminocyclohexane-N, N,N',N'-tetra acetate.

In this connection such a metal complex is denoted by MCy, where M denotes the metal and Cy denotes the remainder of the complex. HCy herein denotes such a complex, where M is replaced by H and with, for example CuCy a complex MCy in which M represents a copper ion. (In these cases the charge symbols are omitted).

A method for differentially kinetic determination of metal ions while using the complex MCy is known. This method is described in Articles by D. W. Margerum et al. in Analytical Chemistry 41, (1969), 226–232 and 233–238.

The known method is based on the exchange of the metal M to be analyzed in the complex MCy for another metal, for example, Cu which in a solution yields the blue complex CuCy. The concentration of the latter complex can be determined spectrophotometrically. Presumably this exchange is not a direct exchange of one metal ion M for another metal ion, in this example a Cu ion, but an exchange effected via an intermediate formation of the compound HCy.

It is assumed that the following reactions take place:

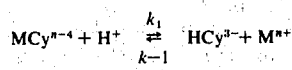

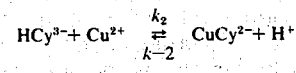

Because of the great stability of $CuCy^{2-}$ as compared with most other MCy complexes and because it is ensured that an excess of $Cu^{2+}$ is present, $HCy^{3-}$ is extracted from equilibrium (1).

Both reactions proceed to the right.

Since under the given circumstances reaction (2) may faster proceed to the right than reaction (1), the latter reaction determines the velocity.

Reaction (1) is a second-order reaction. By maintaining the $H^+$ ion concentration constant during the reaction, it becomes a pseudo first-order reaction and since this reaction determines the velocity, it means that the formation velocity of the complex CuCy in the above-mentioned case is directly proportional to the concentration of the complex MCy. It also means that it makes a quantitative analysis of M possible, if the velocity constant $k_1$ of reaction (1) of the complex MCy at the given temperature and the H+ concentration are known, by spectrophotometrically following the formation of the complex CuCy.

Any metal complex MCy has a characteristic velocity constant $k_1$ at a certain acidity; this constant is independent of other metals present. As a result it is possible to use it in the determination for metals that are present side by side.

However, the velocity constants $k_1$ for reaction 1 of metal complexes MCy of different metals at a given temperature, acidity and ion intensity differ in order of magnitude.

This means that only a limited number of metal combinations can be analyzed when using the said method under the given circumstances of temperature, acidity and ion intensity.

An important factor is particularly the great dependence of the reaction speed of the complexes MCy on the hydrogen ion concentration (acidity, pH). For this reason it is recommended in the known method for determining the velocity constants to carry out calibration runs with the pure components while using a given buffer and ion intensity, and to carry out the determinations while using the same buffer and ion intensity.

In practice this means that a number of individual determinations have to be carried out for determining metals in a mixture of metals. Only one metal or a combination of some metals whose dissociation constants of the complexes MCy differ by less than two orders of magnitude can be determined in one test. Generally, more tests at different acidities will have to be carried out for the analysis of a mixture of metals. This is rather time-consuming.

Furthermore, information is lost because in the known method the acidity of the solution of MCy to be analyzed is brought to such a value that reaction (1) proceeds at a reasonable rate, while measuring is not possible during mixing of the solution of the complex MCy and the buffer solution.

An object of the invention is to provide a method for differentially kinetic determination of metal ions while using one or more complexes MCy in which determinations of metal ions in mixtures are possible without individual tests being required, even when the velocity constants $k_1$ for the reaction (1) of the complexes MCy of the metals in the mixture differ a great deal. The velocity constants $k_1$ for the separate complexes are to be determined in calibration runs.

A further object of the invention is to provide a method in which the components of the measuring solution can be mixed at an acidity at which the speed of the reaction (1) of the complex MCy of the metal M to be determined is substantially zero so as to achieve that no information is lost during the actual measurement. (Measuring solution is herein understood to mean the solution comprising all components present therein during measurement, but in which the acidity is not yet brought to the value required for the actual measurement (still lower acidity)).

Still a further object of the invention is to provide a method in which the use of a stopped-flow apparatus used in known methods is not necessary.

Another object of the invention is to provide a method which, with no stopped-flow apparatus being required, can easily be incorporated in currently used automated equipment for routine determinations of metal ions.

The invention relates to a method for differentially kinetic determination of metal ions in which a solution of a complex MCy, where M represents the metal to be analyzed and Cy has the above-mentioned significance is mixed with a solution in which weak-complexed $Cu^{2+}$ ions are present in an excess relative to the M ions present in the complex MCy, the acidity of the measuring solution thus obtained being increased so as to effect a reaction of the complex MCy and formation of the complex CuCy, the formation of the complex CuCy being measured spectrophotometrically as a function of time, and is characterized in that the acidity of the measuring solution is increased by generating hydrogen ions with the aid of a hydrogen ion generator dissolved in the measuring solution and that the acidity is measured as a function of time.

If in an analysis more metals have to be determined, this can be done in a simple manner by using the method according to the invention because the H ion generation covers an acidity range (pH range) and thus also the range in which the reaction of a given complex MCy and the formation of the complex CuCy are effected at a practical rate.

The method according to the invention is therefore eminently suitable for analyzing a great many mixtures of metals that can form a complex MCy.

Tertiary butylchloride is preferably used as a $H^+$ ion generator. Other suitable $H^+$ ion generators are, inter alia, 2-chloro-2-methylpropanol-1, ethyl chloroformate and sodium pyrosulphate ($Na_2S_2O_7$).

Generation of $H^+$ ions with the aid of the said compounds is based on hydrolysis thereof.

For optimum functioning of a $H^+$ ion generator the medium in which $H^+$ ion generation is effected is preferably adapted in connection with its solubility. When using tertiary butylchloride a mixture of ethanol and water (50% by volume of each) will preferably be used as a solvent. Water is suitable as a solvent for 2-chloro-2-methylpropanol-1 and $Na_2S_2O_7$.

The formation of the blue CuCy complex is determined spectrophotometrically in known manner in the visible spectrum (for example, 700 nm) or in the near ultraviolet spectrum (for example, at 270–310 nm) by means of absorption measurements.

The method according to the invention is started with a solution having a relatively high pH. This pH is chosen to be so high that there is substantially no dissociation of an MCy complex.

The $H^+$ ion concentration is then continuously increased (decrease of the pH) by generation of $H^+$ ions.

During a determination the absorption of the CuCy complex formed and the pH are measured as a function of time ($t$). The variation of the pH with time is shown in FIG. 2 for some examples to be further described hereinafter.

FIG. 1 shows the variation of the absorption as a function of the pH derived therefrom and from measurements of the absorption with the time done on these examples. In this Figure the absorption (A) is plotted vertically and the pH values are plotted horizontally.

When the solution on which the determinations are done comprises complexes MCy of different metals, a curve showing the variation of the absorption with the pH or a superposition of curves is obtained for each complex. The latter is shown in FIG. 1. For a solution comprising the complexes MgCy and ZnCy (concentrations of both: $1.2.10^{-4}$ mol/l) this Figure shows the variation of the absorption (the formation of the complex CuCy) as a function of the pH variation with time (curve 3). (Curves 1 and 2 show the variation of the absorption (A) as a function of the pH for solutions only comprising the complex MgCy and ZnCy, respectively (concentration in both cases: $2.4.10^{-4}$ mol/l)). Curve 4 shows the absorption of a solution of $2.4.10^{-4}$ mol/l CuCy for determining the extinction coefficient of CuCy as a function of the pH with the aid of which curves 1, 2 and 3 can be analysed.

Figure 2:
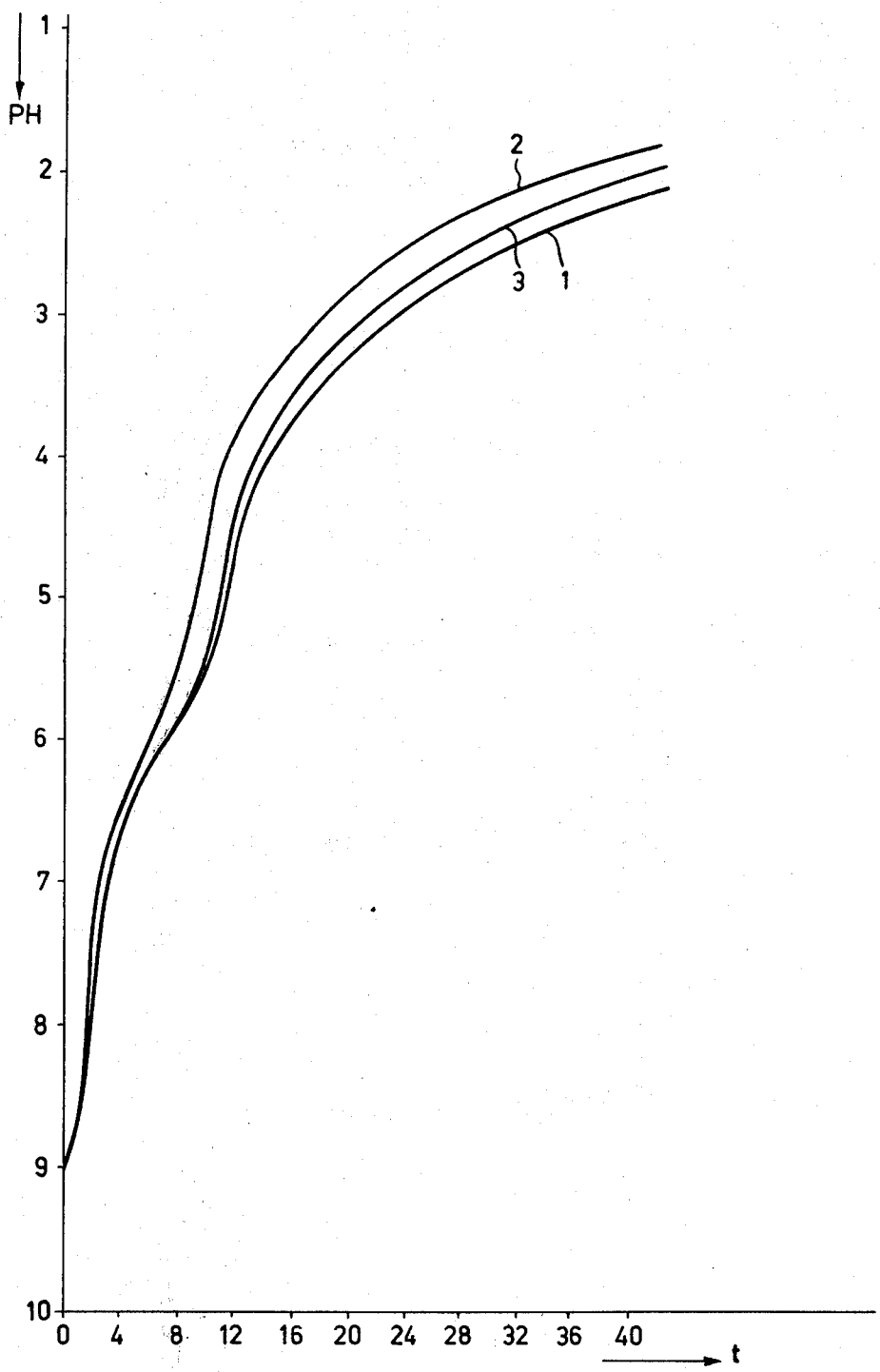

FIG. 2 shows the curves representing, for the determinations referred to in the preceding paragraph, the variation of the pH for solutions of MgCy + ZnCy (curve 3), respectively, as a function of time.

It will hereinafter be described in greater detail by way of a non-limiting example as to how the method according to the invention can be carried into effect.

A complex MCy of a metal (or mixture of metals) to be determined is formed in known manner, for example, by adding a slight excess of $Na_2H_2Cy$ to a solution of the metal ion (or metal ions) to be determined.

A quantity of the obtained solution of the complex MCy is introduced into a spectrophotometer cuvette. If tertiary butylchloride is used as a $H^+$ ion generator, there are also introduced: ethanol and furthermore a copper nitrate solution comprising glycine, sodium perchlorate, propionic acid and sodium hydroxide solution, all this in such a manner that the pH of the solution obtained is approximately 10 and the ethanol content is approximately 50% by volume.

Introduced into a spectrophotometer cuvette having an internal width of 1.0 cm were, for example: 0.5 cubic cm of ethanol, 0.1 cubic cm of tertiary butylchloride, 3.4 cubic cm of a standard copper salt solution (whose composition will be given hereinafter) and 0.1 cubic cm of the solution of the complex MCy to be analyzed. After careful mixing of the contents the cuvette with contents was placed in a holder of a spectrophotometer maintained at a constant temperature. For measuring the pH a conventional glass electrode was placed in the cuvette (for pH measurement).

The standard copper salt solution comprised (per l.) $10^{-3}$ Mol. $Cu(NO_3)_2$, 0.03 Mol. glycine (to prevent precipitation of copper hydroxide), 0.1 Mol. sodium perchlorate and 0.02 Mol. propionic acid and such a quantity of sodium hydroxide that the pH was 10.5. Water-ethanal (55:45% by volume) served as a solvent.

$H^+$ ions are released by hydrolysis of tertiary butylchloride so that the pH decreases. The pH and the formation of CuCy are measured as a function of time (by absorption measurement at 310 or at 700 nm).

When the velocity constants for reaction (1) of components present in the mixture are determined in advance (for which purpose the variation of adsorption and pH of a solution of known concentration must be determined), the concentrations of the metals M to be determined in the sample can be calculated from the variation of absorption and pH with time determined on the sample to be analyzed.

What is claimed is:

1. A method for the differential kinetic determination of metal ions in which a solution of a complex MCy, where M represents the metal to be analyzed and Cy is a complex former is mixed with a solution in which weak-complexed $Cu^{2+}$ ions are present in an excess relative to the M ions present in the complex MCy, the acidity of the resultant mixed solution being increased so as to effect a reaction of the complex MCy and formation of the complex CuCy, the formation of the complex CuCy being measured spectrophotometrically as a function of time, characterized in that the acidity of the measuring solution is increased by generating hydrogen ions with the aid of a hydrolizable hydrogen ion generating compound dissolved in the measuring solution and that the acidity is measured as a function of time.

2. A method as claimed in claim 1, characterized in that tertiary butylchloride is used as a $H^+$ ion generator.

3. A method as claimed in claim 1, characterized in that 2-chloro-2-methylpropanol is used as a $H^+$ ion generator.

4. A method as claimed in claim 1, characterized in that ethyl chloroformate is used as a $H^+$ ion generator.

5. A method as claimed in claim 1, characterized in that sodium pyrosulphate ($Na_2S_2O_7$) is used as a $H^+$ ion generator.

* * * * *